United States Patent [19]

McDonough et al.

[11] Patent Number: 5,236,715
[45] Date of Patent: Aug. 17, 1993

[54] SEX ATTRACTANT FOR THE MINT ROOT BORER

[75] Inventors: Leslie M. McDonough; Harry G. Davis, both of Yakima, Wash.

[73] Assignee: The United States of America as represented by the Secretary of Agriculture, Washington, D.C.

[21] Appl. No.: 826,750

[22] Filed: Jan. 28, 1992

[51] Int. Cl.$^5$ .................. A01N 37/06; A01N 25/10; A01N 25/02; C07C 57/04

[52] U.S. Cl. .................. 424/484; 424/486; 424/501; 424/84; 560/261; 568/903

[58] Field of Search .................. 424/484, 482, 84; 560/261; 568/903

[56] References Cited

U.S. PATENT DOCUMENTS

| | | | |
|---|---|---|---|
| 3,980,771 | 9/1976 | Meijer et al. | 424/84 |
| 4,083,995 | 4/1978 | Mitchell et al. | 514/506 |
| 4,284,622 | 8/1981 | Underhill et al. | 424/84 |
| 4,325,941 | 4/1982 | Dal Moro et al. | 424/84 |
| 4,740,627 | 4/1988 | Byers et al. | 568/485 |

OTHER PUBLICATIONS

H. G. Davis, L. M. McDonough and K. S. Pike, "Attraction of Male *Fumibotys Fumalis* to Females of the Species," *J. Entomol. Soc. Brit. Columbia* 81: 25-28 (1984).

Primary Examiner—Thurman K. Page
Assistant Examiner—E. J. Webman
Attorney, Agent, or Firm—M. Howard Silverstein; John D. Fado; Margaret A. Connor

[57] ABSTRACT

A composition of three compounds, (E,E)-10,12-tetradecadien-1-ol acetate (I), (Z)-11-tetradecen-1-ol acetate (II), and (Z)-9-tetradecen-1-ol acetate (III), in a weight ratio of about 100:18:4 (I:II:III) is a highly effective sex attractant (pheromone) for the male mint root borer. The composition demonstrates biological activity toward mint root borer males comparable to or greater than that of the mint root borer moth females. By attracting adult males to field traps, the composition provides a means for detecting, monitoring, and controlling this agricultural pest.

10 Claims, 2 Drawing Sheets

SEX ATTRACTANT FOR THE MINT ROOT BORER

BACKGROUND OF THE INVENTION

1. Field of the Invention

The invention relates to a novel composition and use thereof for insect control. More particularly, the invention relates to a composition of (E,E)-10,12-tetradecadien-1-ol acetate, (Z)-11-tetradecen-1-ol acetate, and (Z)-9-tetradecen-1-ol acetate, and use of the composition as an attractant, disruptant, and monitoring agent for the mint root borer.

2. Description of the Art

The mint root borer, *Fumibotys fumalis* (Guenee) is a member of the Pyralidae family of the Lepidoptera (moths and butterflies). It is widely distributed in North America (E. Monroe, *Fascicle* 13.2A: 26–28 (1976)). It was first reported to be a pest of a cultivated crop in 1971 when it was found damaging commercially-grown peppermint, *Mentha piperita* L. in the Willamette Valley of Oregon (R. E. Berry, *Ann. Ent. Soc. Amer.* 67: 580–582 (1974)). Subsequently, the mint root borer adapted to and damaged spearmint, *M. spicata* L., and became an established pest in the commercial mint fields of Washington, Idaho, and Oregon (K. S. Pike and M. Glazer, *Journal of Economic Entomology* 75: 1136–1139 (1982)). Damage occurs when the larvae bore into and feed on the mint rhizomes. Infested fields show declining yields and shortened stand life (K. S. Pike et al., *Pacific Northwest Coop. Ext. Pub.* 322 (1988)).

The taxonomy, morphology, and geographical distribution of the mint root borer were described by Monroe, supra. Studies of its biology and behavior (Forbes, Memoir 68, Cornell University Agricultural Experiment Station, Ithaca, N.Y. (1923); Berry, 1974, supra; Berry, Pacific Northwest Cooperative Extension Publication No. 182 (1977); Davis et al., *J. Entomol. Soc. Brit. Columbia* 81: 25–28 (1984); Pike et al., 1998, supra) and chemical and cultural control (Pike, *Insecticide Acaracide Tests* 4: 88 (1979); Pike and Getzin, *Journal of Economic Entomology* 74: 385–388 (1981); Pike and Glazer, 1982, supra) have been reported.

The study by Davis et al., supra, showed that female mint root borers attract males of their species; that males respond optimally to females between 12 midnight and 1 a.m.; that females are attractive at least from 0.5 to 7 days after adult emergence, and that mated females do not attract males during the day following mating.

No single compound or chemical composition was known heretofore to be attractive to this insect species, and no adequate method has been available to determine the presence of the mint root borer prior to crop damage. What is needed is an effective attractant for detecting, monitoring, and controlling this pest.

SUMMARY OF THE INVENTION

We have now surprisingly discovered that a composition of three compounds, (E,E)-10,12-tetradecadien-1-ol acetate, (Z)-11-tetradecen-1-ol acetate, and (Z)-9-tetradecen-1ol acetate, in a particular ratio range, is a highly effective attractant for the male mint root borer. The composition demonstrates biological activity toward mint root borer males comparable to or greater than that of the mint root borer females. The composition of the invention is the first known chemical attractant for the mint root borer and provides, for the first time, a means for detecting, monitoring, and controlling this species.

The composition is highly effective in attracting mint root borer males to traps baited with the composition. An important feature is that it attracts males of the species, and thus is useful for male annihilation. When used in combination with a control agent for the mint root borer, such as a pesticide or biological control agent, the composition can be used to attract and incapacitate male insects so that they are not able to fertilize the females. Another use of the composition of the invention as a control agent is for disruption of mating by confusion of mint root borers.

In sum, the novel sex attractant composition provides a sensitive tool for the detection of the mint root borer and provides a means for population control and population density estimation of this pest. Its usefulness in eliciting a behavioral response when applied to a locus of mint root borer males suggests the following economic applications: (1) the detection of infestation outbreaks; (2) the monitoring of existing adult populations in order to predict future infestation levels for scheduling treatment the following year with larval insecticides or for treatment of moths in the current year with conventional pesticides or other control agents, and (3) the control of reproduction in adult populations either by direct disruption of mating through confusing or inhibitory properties, or by attracting a demographically significant portion of the male population for subsequent destruction or sterilization.

In accordance with this discovery, it is an object of the invention to identify for the first time a unique sex attractant composition for the mint root borer.

Another object of the invention is the provision of the composition as a detection, monitoring, or control agent for the mint root borer.

A further object of the invention is the provision of a mint root borer sex attractant for use with insecticides, biological control agents, or other toxicants to attract and combat the pest.

Other objects and advantages of the invention will become readily apparent from the ensuing description.

DETAILED DESCRIPTION OF THE INVENTION

Figure 1:
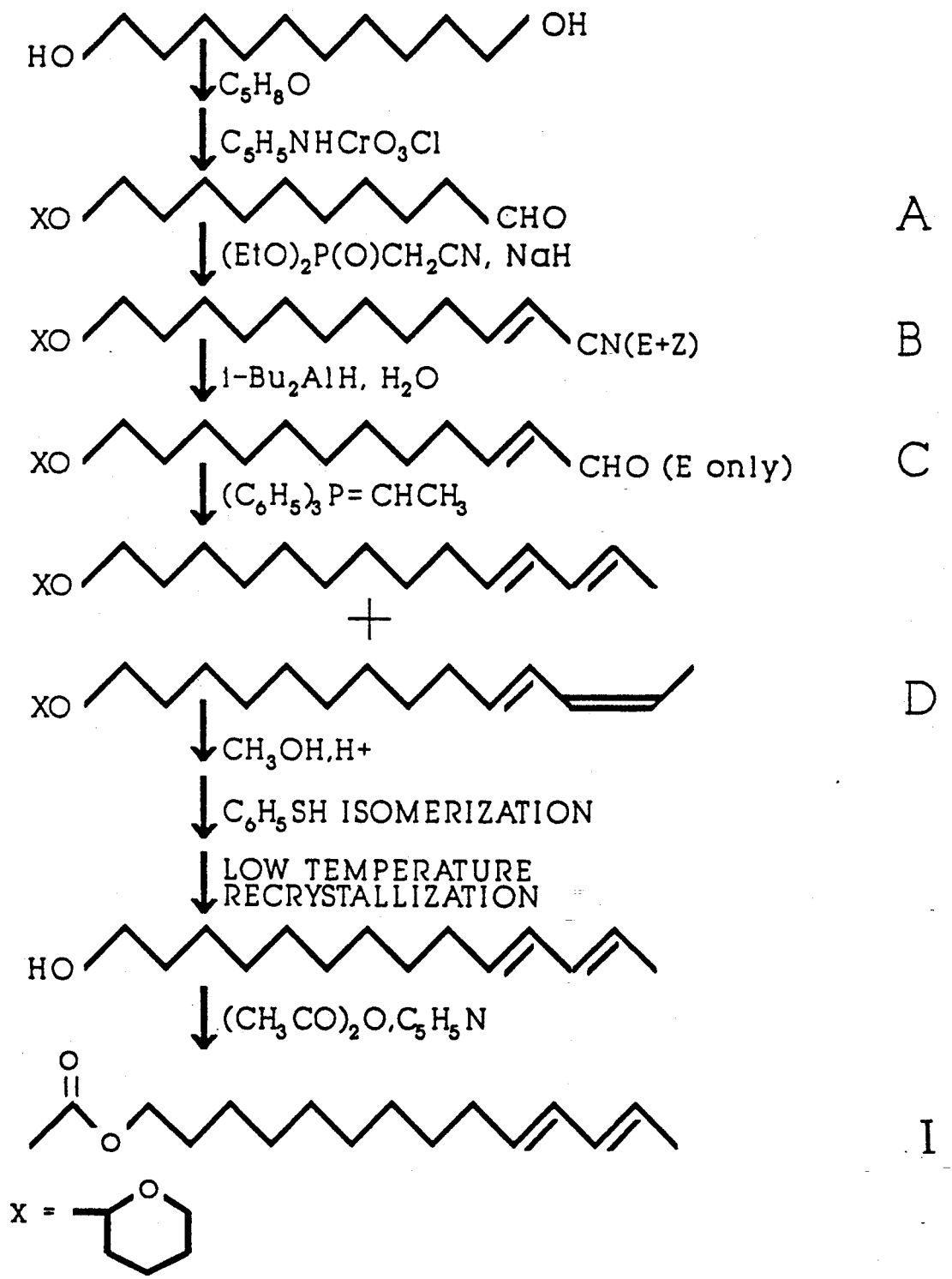
FIG. 1 shows the synthesis of (E,E)-10,12-tetradecadien-1-ol acetate.

The attractant composition of the invention requires the presence of three compounds in the mixture: (E,E)-10,12-tetradecadien-1-ol acetate (hereinafter I), (Z)-11-tetradecen-1-ol acetate (hereinafter II), and (Z)-9-tetradecen-1-ol acetate (hereinafter III). The optimum weight ratio of the compounds in the composition is 100:18:4 (I:II:III). This corresponds to a ratio range of about 100:32:9 (I:II:III) in the evaporating vapor when the composition is used in conjunction with a synthetic elastomer septum as the controlled release substrate.

The weight ratio of the compounds in the composition may be varied. The weight ratio range is 100:9–16:2–8 (I:II:III). This corresponds to a ratio range of about 100:16–28:5–18 (I:II:III) in the evaporating vapor when the composition is used in conjunction with a synthetic elastomer septum as the controlled release substrate.

Compounds II and III in the composition are available commercially or can be prepared synthetically in accordance with the procedure described by S. Voerman in *Agric. Ecosystems Environ.* 21 31–41 (1988). The synthesis of compound I is described in Example 4 below.

The compounds in the three-component attractant composition described above are used in pure or substantially pure form. As used in the specification and the claims, the phrase "pure or substantially pure" means that compounds I, II and III are substantially free of undersirable masking or inhibitory effects with regard to the intended activity. Other compounds may be added to the composition provided they do not substantially interfere with the intended activity of the three-component composition of the invention. For example, as shown in Examples 5 and 6, below, the inclusion of (E)-11-tetradecen-1-ol acetate (IV) with the three-component attractant composition of the invention did not increase or decrease trap catch over that obtained without the inclusion of this compound. The optimum weight ratio of IV in the attractant mixture is 100:18:4:8 (I:II:III:IV). Compound IV may be varied 2-fold in the mixture: 100:18:4:4–16 (I:II:III:IV).

Whether or not a compound interferes with attractant activity can be determined by routine tests in the field as described in Example 6, below. If trap catch is decreased by 2-fold or more when the compound is added to the three-component composition compared to the three-component composition without the added compound, the additive is considered to substantially interfere with attractant activity of the composition.

USE OF THE ATTRACTANT COMPOSITION

The attractant composition of the invention may be used as a detecting agent, monitoring agent, or control agent for the mint root borer. In practice, the attractant composition is used as a trap bait or is otherwise applied to a locus of the mint root borer males, that is, an area where the insects are present or where they may occur, e.g., a mint field. The composition of the invention is used in an amount effective to induce the desired male response. In the case of an attractant response, for example, an effective amount is defined as that quantity of the composition that attracts mint root borer moth males to the location of a bait at a rate significantly higher than males are attracted to a nonbaited location. Under typical field conditions using gray elastomeric septa, the effective amount comprises 1.0 mg to 50 mg of I plus the amounts of II and III required to establish the weight ratio range of 100:9–36:2–8 (I:II:III) or optimum ratio of 100:18:4 (I:II:III). The preferred amount is 3–30 mg of I plus the amounts of the other components necessary to be within the weight ratios specified above. Factors such as population density, temperature, wind velocity, and rain will influence the response of the moths and thus the actual number of males trapped. The amount of composition in a particular set of circumstances that will be within an effective range can readily be determined by a dose response field test as described in Example 6, below.

In the case where the desired response is disruption of mating by confusing or inhibiting the male mint root borer, an effective amount is defined as that quantity of the composition which permeates the atmosphere such that males are prevented from orienting to and inseminating the females, i.e., disruption of mating, at a rate significantly higher than disruption of mating of males at a nontreated location. As with the attractant response, factors such as population density, temperature, wind velocity, and rain will influence the actual number of insects disrupted. The exact dose to use in any particular set of circumstances can readily be determined by a dose response field test.

It is envisioned that the attractant composition would be useful in detecting, monitoring, or controlling mint root borer populations when used in conjunction with a trap or pheromone disseminator (controlled release substrate) known in the art. Exemplary of such traps are the "Pherocon" 1C sticky trap, delta trap, or unitrap. The evaporation rate of the attractant composition is controlled by using a controlled release substrate (CRS). Preferred CRS are gray elastomer septa or other septa devoid of sulfur compounds. Typically, the composition is applied to septa in solution in a suitable carrier, that is, one that does not interfere with the activity of the composition, for example, an organic solvent such as hexane or dichloromethane. Examples of other CRS are laminates, polyvinyl chloride pellets, and microcapillaries.

Optimum attractant amounts can be readily determined by routine experimentation as illustrated in Example 6, below. CRS used for controlling populations by mating disruption include the aforenamed CRS or other CRS specifically designed for this purpose, e.g., Shin Etsu Corp. controlled release dispensers, containing an effective disruptant amount.

When used as a detection or monitoring agent, traps are baited with the novel composition of the invention and the catch tabulated to determine size and location of infestation. Economic use of appropriate pest management systems can then be determined.

Use of the composition as a control agent can be carried out in several ways. One method is to use the composition to attract the insects to suitable substrates and subsequently or simultaneously expose the insects to insecticides which control the mint root borer. An effective amount of the insecticide is used, that is, an amount that is lethal for an exposed insect or at least sublethal but sufficient to incapacitate the insect in regard to mating activity. An example of a useful insecticide is ethoprop ("Mocap" by Mobil Co.). Insecticides can be used in traps baited with the composition. This eliminates the need to spread the insecticides unnecessarily. It is also envisioned that chemosterilants could be used in conjunction with the composition to attract and sterilize male moths.

Another method to control the mint root borer using the composition of the invention is to detect the location and boundaries of localized mint root borer infestations and employ in the area biological control agents such as parasites or predators of the mint root borer.

The attractant composition may also be used to control the mint root borer by confusion of males, thus preventing mating. For example, one technique is to permeate the atmosphere with sufficient compound to prevent males from orienting to and inseminating the females.

DISCOVERY OF THE ATTRACTANT COMPOSITION

Discovery of an attractant for the male mint root borer presented problems of particular difficulty for several reasons including the following: (1) Compounds known to be related to sex pheromones or components of sex pheromones of some of the insects of the Pyralidae family were tested alone and in combination and were shown to be ineffective as a sex attractant for the mint root borer (see Example 1, below). (2) Isolation and identification of putative pheromone components from the mint root borer presented problems of particular difficulty because only small amounts of material could be obtained. This was because no laboratory rearing method for the mint root borer is known, thus it was necessary to dig hibernaculae out of soil of infested fields, and then put them through a program that duplicates hibernation and then emerge them in the laboratory. Further, only a small amount of material was present in each moth, thus investigations were limited to use of gas chromatography-mass spectrometry (GC-MS). The mass spectrum of compound I indicated it was a conjugated tetradecadien-1-ol acetate, that is, one of 36 compounds (9 positions possible for the double bonds and 4 configurations for each position). Elucidation of the double bond position required degradation by ozonolysis and identification of the fragment of I. Elucidation of the configuration required synthesis of the four possible configurations and comparison of GC retention time with that of I. A mass spectral study of female abdominal extracts for compounds with structure related to I was carried out; three tetradecen-1-ol acetates were found. Elucidation of the structures involved synthesis of all 23 possible tetradecen-1-ol acetates, preparation of dimethyldisulfide derivatives and analysis of the derivatives by mass spectrometry. The difficulties encountered in the isolation and identification of sex attractant components of the mint root borer are described in Example 2, below. (3) Preliminary field tests were unsuccessful and directed away from the attractant composition. (4) An electroantennogram (EAG) study of model compounds presented confusing information; it gave so many strong responses that it didn't direct one to specific compounds (see Example 7, below). Thus, identification of I, II, III, and IV was independent of the exploratory EAG studies.

EXAMPLES

The following examples are intended only to further illustrate the invention and are not intended to limit the scope of the invention which is defined by the claims.

EXAMPLE 1

This example describes the attempt to identify the sex pheromone of the mint root borer by testing compounds known to be sex pheromones or components of sex pheromones of the Pyralidae family and related compounds.

In the summers of 1980, 1981, and 1982, (Z)-11-tetradecen-1-ol acetate, (Z,E)-9,11-tetradecadienyl acetate, (Z)-11-hexadecenal, (Z)-9-hexadecenal, (Z)-9-tetradecenal, and (Z)-13-octadecenal were tested for attractancy to the mint root borer in mint fields known to be infested by the insect. These compounds were tested singly and in combinations of two at different ratios and at two different dosages.

Results. None of the traps baited with the test compounds or mixtures caught males of the mint root borer.

EXAMPLE 2

Because of the lack of success of the screening program described in Example 1, the task of isolating and determining the structure of the pheromone from female mint root borers was carried out. This example describes some of the difficulties encountered in the isolation and identification of putative pheromone components from the mint root borer. Because no laboratory rearing method for the mint root borer is known, it was necessary to dig hibernaculae out of soil of infested fields, and then put them through a program that duplicates hibernation and then emerge them in the laboratory.

Mint root borers insects overwinter as larvae in hibernaculae in the soil. The hibernaculae are dirt colored, and it is very laborious to find them. Soil was strained and the pebbles and debris that stay behind were inspected for hibernaculae. During several weeks in the fall of 1982, 400 hibernaculae were collected and placed in peat moss in an insect rearing room. Winter temperatures were simulated until spring (1983), and then the temperature was slowly raised until the insects spun their cocoon, pupated, and subsequently emerged as adults (moths). During this period the colony was checked at regular intervals and emerging moths were collected and placed in individual vials and inspected under a microscope to determine their sex. Female moths produce sex pheromone which they emit from a gland at the end of their abdomen typically for about 2 hours during a 24 hour day. We severed the abdominal ends from female mint root borers during the emitting period and extracted the ends with a solvent. Subsequent tests indicated that the extract contained the sex pheromone. Many extraneous chemicals were also present. To find the pheromone, it was necessary to separate the chemicals in the extract from one another and perform a bioassay to determine which chemicals were part of the pheromone and which were extraneous.

We obtained a gas chromatograph with the ability to separate the chemical constituents in the extract by modifying a Hewlett-Packard (model No. 5711) equipped with megabore capillary columns. A splitter was attached and 90% of the effluent was directed to a heated exit post and collected at intervals. We used an EAG to determine which of the trapped chemical constituents were probably pheromone components and which were extraneous.

Many fractions were collected from the gas chromatograph and one of them produced a stronger EAG response than the others. Another collection of this fraction was analyzed by a gas chromatograph-mass spectrometer. The mass spectrum of the compound (I) in this fraction showed diagnostic peaks which indicated it was a conjugated tetradecadienyl acetate. Thus, it could be one of 44 compounds (11 positions possible for the double bonds and 4 configurations for each position). In order to determine the positions of the double bonds, it was necessary to obtain I in pure form, and then chemically degrade I into fragments by ozonolysis, and then identify the fragments. After purification, 30 ng of I was obtained. After ozonolysis there were too many extraneous materials present to identify the fragment from degradation of I. A greater amount of I was needed for this experiment.

In the fall of 1983, 800 hibernaculae were obtained, and these were reared into adults in the spring of 1984. After purification, 200 ng of I was obtained. This sample was ozonized as in the preceding year, and this time the degradation of fragment of I was identified and indicated the double bonds were in the 10,12 positions. Then the four configurations of 10,12-tetradecadien-1-ol acetate were synthesized, and their gas chromatographic retention times were compared with I. This comparison indicated the double bonds had the E,E- configuration. Therefore the structure of I is E10,E12-tetradecadien-1-ol acetate. This is the first report of the chemical identification of (E,E)-10,12-tetradecadien-1-ol acetate in the female sex pheromone gland of a pyralid.

In an effort to identify other components in the pheromone, we conducted a mass spectral study of extract of female abdominal extracts for compounds with structures related to I. We found three tetradecen-1-ol acetates. There are 23 possible tetradecen-1-ol acetates, only one of which was commercially available. It was necessary to identify the position and configuration of the double bond in each compound. The ozonolysis technique could not be used because there was not enough of these compounds and they could not be separated in pure form from one another. All 23 tetradecen-1-ol acetates were synthesized, and their retention times on polar and non-polar gas chromatographic columns were compared to the tetradecen-1-ol acetates from female mint root borers. These comparisons gave a tentative identification of the tetradecen-1-ol acetates as Z9- (III), E11- (IV), and Z11- (II) tetradecen-1-ol acetates. One or more of these compounds could also be components of the sex pheromone along with I.

Compounds I, II, III, and IV were used as trap bait in rubber septa as a carrier. The dosage was I (100 $\mu$g), II (18 $\mu$g), III (4 $\mu$g), and IV (8 $\mu$g) and represent the same ratios found in the insect. None of the traps baited with this mixture captured male mint root borers even though traps baited with live females did.

No insects were obtained in the fall of 1984. In the fall of 1985, 1000 hibernaculae were obtained. We purified II, III, and IV as a group, prepared the dimethyl disulfide derivatives, and analyzed the derivatives by mass spectrometry. This method verified the identifications we made earlier. Then a high pressure liquid chromatograph was used to purify synthetic I to the 99.2% level. The purified I plus II, III, and IV were again tried in field tests and again with negative results.

In the fall of 1988 we obtained 2000 hibernaculae enabling tests using flight tunnel assays to study male response to natural and synthetic pheromone. No response was obtained using compounds I, III, and IV, tested individually, in flight tunnel tests (Table 1, below) even at high amounts (100 $\mu$g). Compound II was very weakly attractive in these tests. We discovered that positive responses were obtained using a mixture the four-component mixture and a mixture of I, II, and III. Field tests verified this (see Table 2, below). This result indicated the the original structural identifications we made were correct.

EXAMPLE 3

This example describes isolation and identification studies of pheromone components carried out on hibernaculae obtained in 1987, 1988, and 1989.

Insects. Mint root borer hibernaculae containing prepupae were collected from soil samples taken from infested peppermint fields near Harrah, Washington in February and early March in 1987, 1988, and 1989. The hibernaculae were placed in clear-plastic shoe boxes (31×17×9 cm) on a 5- to 6-cm layer of moistened peat moss, covered with clear-plastic lids, and held in a rearing room at a temperature of 12.8° C., RH 55-60%, and a 12:12 hour light-dark cycle. As adults were needed to conduct laboratory or field studies, boxes were removed and placed in another facility at a temperature of 21.1° C. and a 15:9 hour light-dark cycle. The onset of the dark cycle was set at 0800 hr for the flight-tunnel studies and 2100 hr for the field studies. Emergent adults were collected daily at least 1 hour before the dark period and placed in individual vials.

Collection of Pheromone. Female moths (3-4 days old) in their vials were collected 6 hours after the beginning of scotophase and placed in a refrigerator to inactivate them. They were removed individually and their abdominal tips containing the sex pheromone gland (SPG) were severed and steeped for 15-60 minutes in dichloromethane. Then the solution was removed with a syringe. To obtain pheromone that the females may have released while inside the vials, the vials were rinsed with dichloromethane and the rinses were combined.

Gas Chromatography-Electroantennography (GC-EAG). Fractions of extracts from sex pheromone glands or vial washes from vials containing female emissions were collected from a GC equipped with a 0.63-cm-OD×180-cm-long glass column packed with 3% methyl silicone (SE-30) liquid phase on 80-100 mesh "Gas Chrom Q" and connected to an effluent splitter. The initial column temperature was 120° C. for 8 minutes, then programed at 4° C./minute to 210° C. and held at that temperature. The fractions were collected from time zero to the time corresponding to the complete elution of decan-1-ol acetate (10:Ac) and then successively at times corresponding to the complete elution of each of the saturated acetates from undecan-1-ol acetate (11:Ac) through eicosan-1-ol acetate (20:Ac). Fractions were collected in 3-mm-OD, U-shaped, glass traps cooled by Dry Ice-acetone, and then dissolved in dichloromethane and deposited on the inside of glass tubes for EAG determinations. Fractions also were collected for EAG determination from a 0.63-cm-OD×180-cm-long glass column packed with 5% "Carbowax 20M" liquid phase on 80-100 mesh "Gas Chrom Q." Fraction 1 encompassed time zero to the beginning of the elution of 10:Ac; succeeding fractions each encompassed two carbon increments to the beginning of the elution of 20:Ac.

Results of GC-EAG. The EAG response of GC fractions of SPG extract from the methyl silicone column was greatest for the fraction corresponding to the end of tetradecan-1-ol acetate (14:Ac) through the end of pentadecan-1-ol acetate (15:Ac) (1.9 mV vs. 0.1-0.8 mV for the other fractions), and from the "Carbowax" column for the fraction corresponding to the beginning of hexadecan-1-ol acetate (16:Ac) to the beginning of octadecan-1-ol acetate (18:Ac) (0.7 mV vs. 0.2-0.4 mV for the other fractions). The EAG response to GC fractions (methyl silicone column) of the washes of the vials that held females was also greatest for the fraction corresponding to the end of 14:Ac through the end of 15:Ac (0.9 mV vs. 0.05-0.35 mV for the other fractions).

Gas Chromatography-Mass Spectrometry (GC-MS). A Hewlett-Packard (Avondale, Pa.) gas chromatograph (model 5790) with a quadrupole mass spectrometer (model 5970) was equipped with either a DB-1 or DB-Wax capillary column, 60 m×0.25 mm ID (J & W Scientific, Folsom, Calif.). When the pheromone gland extracts were analyzed, the columns were held at 80° for 2 minutes, programmed at 20°/minute to 190° C. for DB-1, and to 200° C. for DB-Wax, and maintained isothermally thereafter. Total ion abundance was monitored. When the dimethyl disulfide derivatives of the monoenes were analyzed, the DB-1 column was used and was held at 80° C. for 2 minutes, programmed at 20°/minute to 255° C. and held at that temperature for 30 minutes.

Determination of Double Bond Position of Monoenes. Monoenes from extract of sex pheromone glands were provisionally identified by comparing retention times on DB-1 (60 m×0.25 mm ID; 2 minutes at 80° C. then 20°/minute to 190° C.) and DB-Wax (45 m×0.20 mm ID at 145°) GC capillary columns with synthetic monoenes. A Hewlett-Packard model 5880 GC was used.

Rigorous determination of double bond positions was accomplished by mass spectral determinations of fragmentation patterns of the dimethyl disulfide (DMDS) derivatives, (H. R. Buser et al. *Analytical Chemistry* 55: 818–822 (1983)). To prepare the derivatives, monoenes (15 ng) isolated as a GC fraction from extract of SPG in 200 μl of dichloromethane were transferred to a 1-ml "Reacti-vial" (Pierce Chemical Co., Rockford, Ill.). The solution was evaporated just to dryness in a stream of nitrogen, and the residue was dissolved in 50 μl heptane. Then 50 μl DMDS and 10 μl of a saturated solution of iodine in ether were added. The vial was sealed and heated overnight at 40° C. in a convection oven. The solution was diluted with 200 μl of heptane and excess $I_2$ was removed by shaking with 100 μl of 5% of sodium bisulfite solution. The heptane solution was removed with a syringe and concentrated to 2 μl for injection into the GC-MS.

Determination of Positions and Configurations of Double Bonds of Diene. The GC purified diene (144 ng) was ozonized in predistilled dichloromethane at −70° C. with an ultraviolet ozonizer (Orec Co. model 03V1, Phoenix, Ariz.), and the ozonide was reduced with a triply recrystallized triphenylphosphine. The ozonized sample was injected on a GC column (DB-1, 60 m×0.25 mm) which was held at 80° C. for 7 minutes, programmed at 6°/minute to 200° C. and held at that temperature. When the configuration of the diene was determined, the same column was held at 80° C. for 2 minutes and programmed at 20°/min to 180° C. and held at that temperature.

Results. GC-MS analysis (DB-1 column) of SPG extract (50 female equivalents) at the retention time period that produced the strong EAG response indicated the presence of a tetradecadienyl acetate [$M^+$, 252; $(M-60)^+$, 192; $CH_3CO_2H_2^+$, 61] at a retention index ($I_x$) of 1838. Also, eluting prior to the tetradecadienyl acetate were three tetradecenyl acetates [$(M-60)^+$, 194; $CH_3CO_2H_2^+$, 61] at $I_x$ values of 1776, 1781, and 1788. There was about 0.5 ng of the diene per female equivalent, and the ratio of the monoenes to the diene for each $I_x$ value was 0.04:1 (1776), 0.08:1 (1781), and 0.18:1 (1788).

Positions and Configurations of Double Bonds of Pheromone Gland Components. Ozonolysis of the diene gave a single GC peak (methylsilicone column) with a retention time of 24.50 min near that of hexadecane (retention time=24.77 min) and the same within experimental error (±0.04 min) as the ozonolysis product of 10,12-tetradecadien-1-ol acetate (retention time=24.52). The configuration of the diene was EE (retention time=21.85 min) and the retention times of the four isomers of a synthetic standard (McDonough et al., 1982, supra) were: ZE, 21.33; EE, 21.85; EZ, 22.10; ZZ, 22.29.

A comparison of retention times of the pheromone tetradecen-1-ol acetates with those of the synthetic tetradecen-1-ol acetates on polar and nonpolar capillary GC colums indicated the pheromone tetradecen-1-ol acetates were Z9, Z11, and E11. Mass spectral analysis of the DMDS derivatives confirmed these assignments. The monoene derivatives and their diagnostic peaks (Buser et al., supra) were: Z9-[$M^+$, 348 (33%); A, 117 (53%); B 231 (100%)]; Z11-[$M^+$, 348 (21%); A, 89 (34%); B 259 (100%)]; E11-[$M^+$, 348 (19%); A, 89 (25%); B, 259 (100%)]. The retention times of the DMDS derivatives (in minutes) were: Z9-, 25.34; Z11-, 27.12; E11-, 27.54. The configurational assignments were confirmed by comparison of retention times with synthetic samples (E9-DMDS derivative at 25.66 min).

EXAMPLE 4

Synthesis of (E,E)-10,12-tetradecadien-1-ol Acetate (I).
The synthesis of I is shown in FIG. 1.

10-[Tetrahydro-2H-pyran-2-yl)oxy]decanal (A) was prepared as reported by McDonough et al., 1982, supra. To prepare 12-[tetrahydro-2H-pyran-2-yl)oxy]-2-dodecenenitrile (B), a mixture of 2 g (66 mmol) of NaH (80% dispersion in oil) in 90 ml anhydrous ether and 30 ml dry tetrahydrofuran was chilled and stirred under nitrogen in an ice bath. Diethylcyanomethylphosphonate (11.7 g, 66 mmol) in 10 dry ether was added dropwise; a thick salt formed. After the addition was complete, the mixture was stirred for 1 hour at room temperature, and then cooled to below 15° C. The decanal (A) (7.7 g, 30 mmol) in 10 ml anhydrous tetrahydrofuran was added dropwise during about 30 minutes, and the mixture was stirred vigorously at room temperature for 2 hours. After the reaction mixture was quenched with methanol (1.5 ml), the solution was concentrated with a rotary evaporator and extracted with water (100 ml). The water and organic phases were separated, and the water phase was extracted three times with ether. The combined ether and organic phases were extracted once with water, then with saturated sodium chloride solution, and then dried with sodium sulfate. The solution was filtered, and the solvent was removed by a rotary evaporator, giving 10.1 g crude product (5.2 g of (B) by GC analysis) which was purified by liquid chromatography (elution from silica gel with 15% ether/hexane). IR: 2180 cm$^{-1}$, nitrile; 1620 cm$^{-1}$, double bond; typical tetrahydropyranyl ether pattern from 1470 to 1250 cm$^{-1}$. GC-MS: base peak m/z=85 (pyran fragment); m/z=101 and 178, typical of pyran fragmentation; 278 (M-1) and 279 ($M^+$). The yield of purified product was 4.8 g (57%).

To prepare 12-[tetrahydro-2H-pyran-2-yl]-2-dodecenal (C), 5 ml (28.5 mmol) of diisobutylaluminum hydride in 20 ml anhydrous hexane was added dropwise during 30 minutes to a stirred solution of 4.8 g (17.2 mmol) of (II) at −10° C. in 75 ml anhydrous hexane under argon. After the solution was stirred for 3 hours at −10° C. and 1 hour at 0° C., it was cooled to −10° C. and 1 ml isopropanol was added dropwise, and then 6 ml water was added dropwise. The resultant mixture was poured over a stirred mixture of 25 g ice and 7.6 ml acetic acid. After the mixture was stirred vigorously for 10 minutes, the aqueous and organic phases were separated, and the aqueous phase was extracted with hexane. The hexane extracts and the organic phase were combined and washed successively with 1N hydrochloric acid, water, saturated sodium bicarbonate, and saturated sodium chloride solution. The solution was dried over sodium sulfate. Solvent was removed with a rotary evaporator giving 5.1 g of crude (C). IR: 2700 cm$^{-1}$ (w)

and 1690 cm$^{-1}$ (s), aldehyde; 1630 cm$^{-1}$, double bond; typical tetrahydropyranyl ether pattern from 1470 to 1250 cm$^{-1}$. GC-MS: one GC peak showing typical MS pyran fragmentation: 85 (base peak), 101, 181; and 281 (m−1). GC analysis showed one peak corresponding to 3.5 g of product 72% yield).

To prepare 1-[(tetrahydro-2H-pyran-2-yl)oxy]-10,12-tetradecadiene (D), ethyltriphenylphosphonium bromide (15.8 g, 42.5 mmol) in 270 ml dry tetrahydrofuran was stirred in a three-neck flask under nitrogen at room temperature for 30 minutes. The bromide did not completely dissolve. n-Butyllithium (27.4 ml of 1.6M in hexane, 43.8 mmol) was added by syringe through a rubber septum on one neck of the flask. The solution formed the deep red color of ethylidenetriphenyl phosphorone, and the remainder of the bromide dissolved. The dodecenal (C) (5.1 g crude, 3.5 g actual) in 40 ml tetrahydrofuran was added dropwise, and the mixture was stirred for 1 hour after the addition was complete. Excess phosphorane was discharged with acetone, and the solvent was removed on a rotary evaporator. The residue was extracted with water and pentane. Combined pentane fractions were dried over sodium sulfate. The pentane was removed on a rotary evaporator leaving 5.6 g crude product oil.

To prepare (E,E)-10,12-tetradecadien-1-ol acetate (I), the tetradecadiene (D) (5.6 g) in 200 ml methanol containing eight drops concentrated HCl was refluxed for 15 minutes. After the solution was cooled, 400 ml of water was added, and the mixture was extracted three times with hexane. The hexane extract was dried over sodium sulfate, and the hexane was removed with a rotary evaporator leaving 3 g crude 10,12-tetradecadienol, which was purified by silica gel liquid chromatography. Unwanted side products were eluted with 10% ether/hexane, and the alcohol was eluted with 50% ether/hexane, giving 2.4 g (66% yield based on the dodecenenitrile (B)).

The 2.4 g of tetradecadienol was dissolved in 55 ml of pentane containing 30 μl of thiophenol in a 100-ml round bottom flask. The flask was heated with a water bath, and the pentane was distilled off. Then a reflux condenser was connected to the flask, and the mixture was heated at 100° C. for 2 hours. The residue was dissolved in 600 ml of heptane which was removed by a rotary evaporator. The thiophenol was removed simultaneously. The yield of isomerized tetradecadienol was 2.01 g (84%). The isomer content by GC analysis was 62% EE, 19% EZ, 15% ZE, 4% ZZ. The tetradecadienol was recrystallized twice at low temperature from pentane to give 0.83 g of a product of 96.2% EE. 10,12-Tetradecadienol in 75 ml pyridine and 5 ml acetic anhydride was refluxed 1.5 hours. After the solution was cooled, 200 ml hexane was added, and the mixture was extracted successively with water, 6N hydrochloric acid (twice), and water. The pentane phase was dried over sodium sulfate, filtered, and the pentane was removed by rotary evaporation, leaving crude product, which was purified by silica gel liquid chromatography (elution in 10% ether/hexane); the yield was 1.0 g (94% based on the alcohol).

EXAMPLE 5

This example describes the study of the response of adult male mint root borers in a flight tunnel to pheromone components and combinations of the components.

Compounds I, II, III, and IV were tested individually at levels of 100 μg. The four-component composition having a ratio of 100:18:4:8 (I:II:III:IV) was tested at several dose levels. The three-component composition having a ratio of 100:18:4 (I:II:III) was tested.

A flight tunnel constructed as described by J. R. Miller and W. L. Roelofs (Journal of Chemical Ecology 4: 187–198 (1978)) was used. The flight tunnel room was maintained at 22° C. Males were released in groups of five. The number of males initiating and sustaining flight and contacting the lure were determined. All lures were formulated in gray elastomeric septa (D. F. Brown and L. M. McDonough, Journal of Economic Entomology 79: 922–927 (1986)) to prevent isomerization of the diene. Males were three to four days old and were maintained on a reverse dark-light cycle (10 and 14 hours). Tests were conducted 3 hours after the onset of scotophase.

Results. The results are presented in Table 1, below. As can be seen from the data, no response was obtained using compounds I, III, and IV, tested individually; compound II was very weakly attractive (Table 1, tests 1–4). When the four components were tested in the ratio of 100:18:4:8 (I:II:III:IV) and the dosage of EE was 100 μg (the same as the unsuccessful field test), 65% of males exhibited upwind flight and 50% touched the source (test 5). Lower doses of 33 and 10 μg of this ratio produced less response (tests 6 and 7), while a higher dose produced the highest percent responding (test 8). Subtraction of IV from the blend produced a response almost equivalent to the four-component mixture (test 9 vs. 5).

TABLE 1

| Test | Lure (dose in micrograms) | Number of males tested | Number flying upwind | Number contacting source |
|---|---|---|---|---|
| 1 | (E,E)-10,12-tetradecadien-1-ol acetate (I) (100) | 10 | 0 | 0 |
| 2 | (Z)-11-tetradecen-1-ol acetate (II) (100) | 10 | 3 | 1 |
| 3 | (Z)-9-tetradecen-1-ol acetate (III) (100) | 10 | 0 | 0 |
| 4 | (E)-11-tetradecen-1-ol acetate (IV) (100) | 10 | 0 | 0 |
| 5 | I (100) + II (18) + III (4) + IV (8) | 20 | 13 | 10 |
| 6 | I (33) + II (6) + III (1.3) + IV (2.7) | 10 | 5 | 3 |
| 7 | I (10) + II (1.8) + III (0.4) + IV (0.8) | 10 | 2 | 2 |
| 8 | I (300) + II (54) + III (12) + IV (24) | 5 | 4 | 4 |
| 9 | I (100) + II (18) + III (4) | 10 | 6 | 4 |

EXAMPLE 6

Field Tests. Compounds II, III, and IV used for the field tests were obtained from commercial sources and were pure by GC analysis and contained less than 1% of the geometric isomer. Compound I was synthesized by a modification of the method for Amorbia cuneana (McDonough et al., Journal of Chemical Ecology 8: 255–265 (1982); McDonough and Smithhisler, Southwest. Entomol. 14: 153–157 (1989)) as described above. Isomeric purity was 98.5% EE, 1% EZ, and 0.5% ZE for all of the experiments except the one in which the effect of purity was tested. Then the purity was 96.0% EE, 2.5% EZ, and 1.5% ZE. Candidate lures in 100 μl of dichloromethane were impregnated into gray elastomeric septa; dichloromethane alone was added to control septa. "Pherocon" IC sticky traps (Trece Corp., Salinas, Calif.) were used. Traps were suspended from a movable metal arm (an 18×23-cm shelf bracket) attached by a metal hose clamp to a 120-cm-long wooden broom handle driven into the ground. This arrangement enabled the traps to be positioned just above the mint foliage, usually 45-60 cm above the ground, where most flight activity was believed to occur.

The position of each trap in the experimental plot was drawn randomly and traps were deployed at approximately 10-m intervals. Females used in the field tests were placed in aluminum wire screen cages (9×9×2 cm, three females/cage), which were suspended by a wire from the top of the trap equidistant between the top and bottom. There were four replicates of each lure tested and the trap data were transformed by $(x+0.5)^{\frac{1}{2}}$ and compared by Duncan's (*Biometrics* 11: 1-41 (1955)) multiple-range test (P=0.05).

Results. In an early field test, lures containing 100 μg of I plus 18, 4, and 8 μg of II, III, and IV, respectively, were tested in a mint field (four replicated traps per test). Total male captures (13) were not statistically different from blank traps but captures in female baited traps (98) were.

In further field tests (Table 2, test 1) when the ratio of I:II:III was 100:18:4: and the dose of I was varied from 100 to 3000 μg, the 300-μg dose produced significant trap catch compared to controls and was equivalent to that produced by females. In test 2 (Table 2) captures produced by the lower doses were statistically significant and the 10 mg dose was equivalent to females. Test 3 was conducted to determine if a higher proportion of II would increase catch. At neither the 3- nor the 10-mg dose level did the increase in the proportion of II produce statistically significant increases in trap catch.

Collectively, these experiments demonstrated that the three- or four-component lure in the ratio found in the sex pheromone gland and at a dose of 3-10 mg of I in gray elastomeric septa produced a viable attractant, competitive with female baited traps in field tests.

TABLE 2

| Test No. | Lure | Dosage (microgm/septum) | Cumulative Captures |
|---|---|---|---|
| 1 | July 27-28, 1989 | | |
| | I + II + III | 100:18:4 | 9a |
| | I + II + III | 300:54:12 | 5a |
| | I + II + III | 1000:180:40 | 22a |
| | I + II + III | 3000:540:120 | 68b |
| | 3 Females | | 61b |
| | Blank septa | | 4a |
| 2 | August 4-6, 1989 | | |
| | I + II + III | 3000:540:120 | 105a |
| | I + II + III | 3000:540:120[a] | 128a |
| | I + II + III | 10000:1800:400 | 278b |
| | I + II + III + IV | 3000:540:120:240 | 119a |
| | 3 Females | | 329b |
| | Blank septa | | 14c |
| 3 | August 8, 1989 | | |
| | I + II + III | 3000:1800:120 | 125ab |
| | I + II + III | 3000:5400:120 | 61ac |
| | I + II + III | 10000:1800:400 | 100b |
| | I + II + III | 10000:5400:400 | 164b |
| | 2 Females | | 31c |
| | Blank septa | | 4c |

[a]The isomeric purity of I in this test was 96%; in all other tests isomeric purity was 98.5%.

EXAMPLE 7

This example describes a study of electroantennographic responses of male mint root borers to model compounds.

Electroantennogram (EAG) Determinations. EAG determinations of model compounds were made with the apparatus described in McDonough et al. *Journal of Chemical Ecology* 6: 565-572 (1980) except that 60 μg charges were used. Duplicate determinations were made of each compound. The model compounds were obtained commercially or were prepared and purified by established synthetic methodology, mainly by the procedure of Voerman, supra. All compounds were at least 98% pure by capillary gas chromatographic analysis, and contained 1% or less of their geometrical isomers. The compounds used were: all of the saturated and monoene 12- and 14-carbon alcohols and corresponding acetates; Z and E isomers of 7-, 9-, and 11-hexadecen-1-ol acetates; Z and E isomers of 7-, 8-, and 9-dodecenals; (Z)-7-tetradecenal; (Z)-9-tetradecenal; (Z)-11 and (E)-11-tetradecenal; (Z)-5-hexadecenal; (Z)-7- and (E)-7-hexadecenal; (Z)-9-hexadecenal; (Z)-11- and (E)-11-hexadecenal; and (Z)-13-hexadecenal.

Figure 2:
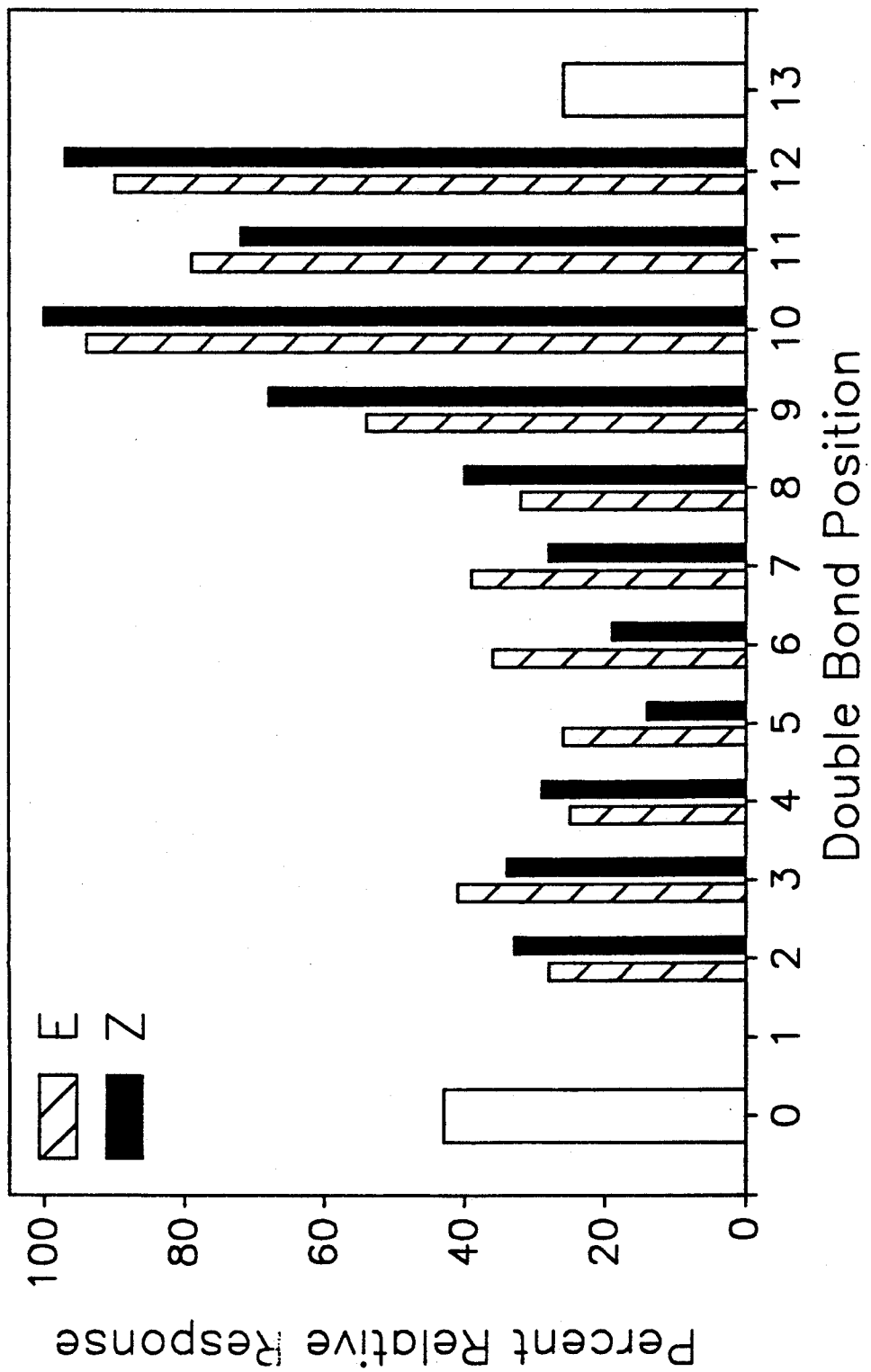
FIG. 2 shows the electroantennographic responses of male mint root borers to 14-carbon acetates. Numbers indicate double-bond position; zero indicates saturated.

Among the model compounds tested, the strongest EAG responses were obtained from the 14-carbon acetates (FIG. 2). The 10 and 12 positions of unsaturation produced the strongest responses, and strong responses were also obtained from the 9 and 11 positions. After the 14-carbon acetates, the strongest responses were obtained from the 12-carbon acetates: (E)-10- and (Z)-10-dodecen-1-ol acetates produced responses of about 50% of the standard ((Z)-10-tetradecen-1-ol acetate) and the other positional isomers produced responses of about 25% of the standard. Other tested compounds produced responses of 0-30% of the standard.

The EAG results were confusing as so many compounds gave strong responses, and thus, did not direct us to specific compounds.

It is understood that the foregoing detailed description is given merely by way of illustration and that modification and variations may be made within without departing from the spirit and scope of the invention.

Having thus described the invention, we claim:

1. An attractant composition for mint root borer males, which comprises a mixture of pure or substantially pure (E,E)-10,12-tetradecadien-1-ol acetate (I), pure or substantially pure (Z)-11-tetradecen-1-ol acetate (II), and pure or substantially pure (Z)-9-tetradecen-1-ol acetate (III), in a weight ratio of about 100:9-36:2-8 (I:II:III).

2. The composition of claim 1 wherein said weight ratio is about 100:18:4 (I:II:III).

3. The composition of claim 1 which further includes (E)-11-tetradecen-1-ol acetate (IV) in weight ratio of 100:18:4:4-16 (I:II:III:IV).

4. The composition of claim 1 which further includes an organic solvent as a carrier for said composition.

5. The composition of claim 1 in combination with an effective insecticidal amount of an insecticide for the mint root borer.

6. A method of attracting male mint root borers, which comprises placing in a locus of male mint root borer moths a controlled release substrate (CRS) having an effective attractant amount of a composition comprising pure or substantially pure (E,E)-10,12-tetradecadien-1-ol acetate (I), pure or substantially pure (Z)-11-tetradecen-1-ol acetate (II), and pure or substantially pure (Z)-9-tetradecen-1-ol acetate (III), in a weight ratio of about 100:9-36:2-8 (I:II:III).

7. The method of claim 6 wherein said weight ratio of said composition is about 100:18:4 (I:II:III).

8. The method of claim 6 wherein said CRS is a synthetic elastomer septum.

9. A method of disruption of mating of mint root borer moths, which comprises applying to the locus of male mint root borer moths an effective disruptant amount of the composition of claim 1.

10. A method for trapping male mint root borer moths, which comprises baiting a trap with an effective attractant amount of the composition of claim 1.

* * * * *